(12) United States Patent
Pedrazzini

(10) Patent No.: US 9,481,528 B2
(45) Date of Patent: Nov. 1, 2016

(54) TEMPORARY PARKING STATION FOR CONVEYING DEVICES OF BIOLOGICAL PRODUCT CONTAINERS

(71) Applicant: Inpeco Holding Ltd., Qormi (MT)

(72) Inventor: Gianandrea Pedrazzini, Paradiso (CH)

(73) Assignee: INPECO HOLDING LTD., Qormi (MT)

( * ) Notice: Subject to any disclaimer, the term of this patent is extended or adjusted under 35 U.S.C. 154(b) by 129 days.

(21) Appl. No.: 14/412,253

(22) PCT Filed: Jul. 10, 2013

(86) PCT No.: PCT/EP2013/064561
§ 371 (c)(1),
(2) Date: Dec. 31, 2014

(87) PCT Pub. No.: WO2014/009407
PCT Pub. Date: Jan. 16, 2014

(65) Prior Publication Data
US 2015/0192599 A1    Jul. 9, 2015

(30) Foreign Application Priority Data

Jul. 12, 2012 (IT) .............................. MI2012A1218

(51) Int. Cl.
| | |
|---|---|
| *B65G 47/69* | (2006.01) |
| *G01N 35/04* | (2006.01) |
| *B65G 47/26* | (2006.01) |
| *B65G 47/51* | (2006.01) |

(52) U.S. Cl.
CPC ............. *B65G 47/69* (2013.01); *B65G 47/261* (2013.01); *B65G 47/5113* (2013.01); *B65G 47/5118* (2013.01); *G01N 35/04* (2013.01); *G01N 2035/0406* (2013.01); *G01N 2035/0465* (2013.01); *G01N 2035/0493* (2013.01)

(58) Field of Classification Search
CPC .............. B65G 47/69; B65G 47/5113; B65G 47/5118
USPC ....... 198/347.1, 351, 364, 368, 370.01, 426, 198/431
See application file for complete search history.

(56) References Cited

U.S. PATENT DOCUMENTS

| | | | | |
|---|---|---|---|---|
| 1,474,619 | A | * | 11/1923 | Buck .............................. 198/431 |
| 1,481,542 | A | * | 1/1924 | Dunsieth, Jr. ................ 198/431 |
| 3,604,551 | A | * | 9/1971 | Fink ............................. 198/448 |
| 4,518,264 | A | | 5/1985 | Nohso |

(Continued)

FOREIGN PATENT DOCUMENTS

| | | |
|---|---|---|
| WO | 96/25712 A1 | 8/1996 |
| WO | 2010/015486 A1 | 2/2010 |
| WO | 2013/072318 A1 | 5/2013 |

*Primary Examiner* — Leslie A Nicholson, III
(74) *Attorney, Agent, or Firm* — Jacobson Holman, PLLC.

(57) ABSTRACT

A temporary parking station of conveying devices containing only one container of biological, products is described, interfaced with a laboratory automation system, comprising a conveyor belt with at least one dispatching lane with a stop gate adapted to queue the conveying devices let into the station and to release only one of said conveying devices at each step to a diverter fitted on a motorized belt, parallel to the dispatching lane, adapted to move said diverter in steps in either one direction or the other from a start of travel position to an end of travel position, diverting in steps only one at a time said conveying devices on a main conveyor belt moveable in a direction perpendicular to the motorized belt.

5 Claims, 4 Drawing Sheets

(56) References Cited

U.S. PATENT DOCUMENTS

Figure 1:
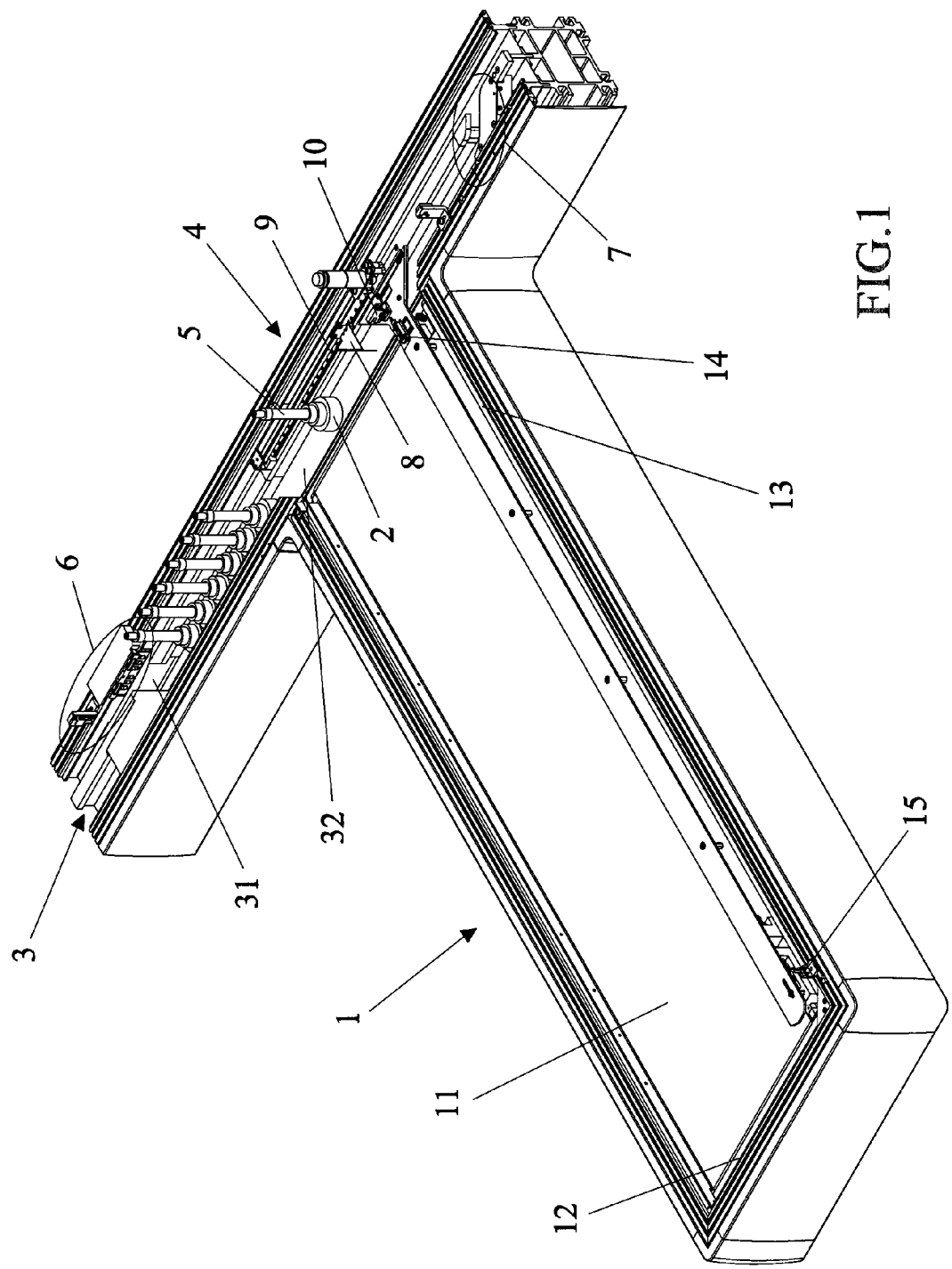

| | | | |
|---|---|---|---|
| 5,769,204 A * | 6/1998 | Okada et al. | 198/443 |
| 5,918,723 A * | 7/1999 | Schuitema et al. | 198/347.4 |
| 5,972,295 A | 10/1999 | Hanawa et al. | |
| 6,056,107 A * | 5/2000 | Schuitema et al. | 198/347.4 |
| 6,269,933 B1 * | 8/2001 | Schuitema et al. | 198/446 |
| 6,355,488 B1 | 3/2002 | Rousseau et al. | |
| 6,458,324 B1 | 10/2002 | Schinzel | |
| 6,520,313 B1 | 2/2003 | Kaarakainen et al. | |
| 6,622,847 B2 * | 9/2003 | Schuitema et al. | 198/399 |
| 2004/0159589 A1 | 8/2004 | Matsumoto | |
| 2005/0271555 A1 | 12/2005 | Itoh | |
| 2014/0001008 A1 * | 1/2014 | Steeber | 198/347.1 |

* cited by examiner

TEMPORARY PARKING STATION FOR CONVEYING DEVICES OF BIOLOGICAL PRODUCT CONTAINERS

The present invention relates to a temporary parking station for conveying devices of biological product containers.

Nowadays, in the field of conveying biological product samples in test laboratories, the need to integrate the highest number of test modules along the entire automation system is increasingly more felt, to make the laboratory as complete as possible with regards to the various types of tests which can be performed on the samples and to dispatch the samples to the various test modules which interface with the conveyor belt crossing the entire laboratory.

Therefore, the conveyor belt typically interfaces with a high number of such test modules arranged in series along the automation system. Each test module accommodates, processes and, after processing, expels such containers of biological products or test tubes, appropriately accommodated in specific conveying devices.

Obviously, pre- or post-test modules used to perform the operations on test tubes which are required during the flow of samples on the conveyor belt from one module to the other (loading/unloading, uncapping/recapping, separation or centrifugation of contents, and so on) are also present along the automation system together with the modules actually used for testing.

Each of the concerned modules may have a different working frequency on each single sample, and it stands to reason that problems related to the accumulation of queues of conveying devices (either containing test tubes or possibly empty) may occur, typically because a machine which is particularly slow in processing each single sample is preceded by another module which instead processes them very rapidly, thus making a quantity of conveying devices available upstream of the slower machine at a frequency that the machine cannot handle.

This inevitably slows down or causes irregularities in the flow of conveying devices along the automation system because of the presence of one or more slow machines which form 'bottlenecks' in the system.

It is therefore necessary to avoid the accumulation of conveying devices of modules which process samples particularly slowly, and therefore by extension along some points of the automation system.

A solution may consist in making the conveying devices proceed along the automation system so that they pass the slow module and are dispatched to it only once it is free, i.e. once the queue upstream of the module has been cleared, either entirely or at least in part. Thus, typically, such conveying devices additionally circle once or more about the entire automation system until they turn up at the interface with the concerned module, which can now accommodate them, again. The aforesaid conveying devices could be accommodated in identical modules if one or more are present along the automation system and free instead; if no such modules are present, the conveying devices keep circulating along the automation system, and during the supplementary circle cannot undergo operations by other modules, thus essentially occupying room unnecessarily along the automation system.

In order to overcome this problem, temporary storage devices of samples exist in the laboratory automation systems, into which the samples can be unloaded for a given period of time while they are waiting to be taken by the appropriate module. An apparatus of this type is described, for instance, in patent application PCT/EP2009/058886 by the Applicant, i.e. a loading/unloading bench of samples to/from an automation system which therefore works in two-way manner, and to which reference is made for a more detailed description of some construction details.

However, the known storage benches are rather bulky apparatuses; typically, due to the space that they occupy and the fact that they are sophisticated and, therefore rather costly, there are only few (often only one) of them in an automation system. It stands to reason that, examining the unloading operation only, conveying test tubes which will then be dispatched to different modules once the modules are cleared into this single storage area may imply that the test tube is far from the module to which it is dispatched, even after leaving the bench and returning to the automation system.

U.S. Pat. Nos. 5,972,295, 6,355,488 B1, 4,518,264 and 6,458,324 B1 describe a temporary parking station for conveying devices of a plurality of biological product containers interfaced with a laboratory automation system.

Furthermore, during the unloading operation of samples from the automatic conveyor of the automation system to the storage bench, the test tube is picked by a gripping device and thus separated—disassociated—from the conveying device. When it is later reintroduced along the system, a new association with the conveying device taking it is created; this operation may certainly cause, in case of faults or malfunctions of any type, association errors between conveying device and test tube.

Similarly, the number of empty conveying devices, which are not conveying a test tube, circulating along the automation system is often higher than the system needs. This is not very efficient because it is an unnecessary occupation of resources and space along the system, and it would be preferable to park these conveying devices temporarily as well.

It is the object of the present invention to make a temporary parking station of conveying devices which accommodate test tubes to prevent them from performing supplementary circles about the automation system only because the module which must process them is momentarily occupied, even more so that, once such a module clears, it could immediately accommodate new samples to be processed but the samples could be instead at that point in a zone of the conveyor belt very far from the module precisely they were because previously dispatched to continue along the automation system during the wait A further object of the prevent invention is to make a temporary parking station of conveyor devices containing test tubes from which the conveying devices may be called up at any time to be dispatched rapidly to the appropriate module, said conveying devices being either full or empty, i.e. allowing to dispatch the conveying devices to other modules arranged along the automation system which could need them.

A yet further object of the present invention is to make a temporary parking station of conveying devices which is less bulky, and thus simpler to make (and less costly) than the known system so as to be able to position a high number of instances along a single system, each of which being as close to the module to which it is essentially combined as possible.

A not last object of the present invention is to make a parking station capable of ensuring in all cases a high capacity so as to respond to the increasingly growing operative volumes of a test laboratory in terms of number of conveying devices/test tubes in hand.

The objects of the present invention include making a parking station in which the conveying devices with test tube do not need to be disassociated from the conveying device during the waiting time in the station, in order to avoid possible errors in the subsequent re-association which occur in the known solutions.

In accordance with such objects, the invention is reached by a temporarily parking station as described in claim 1.

Figure 2:
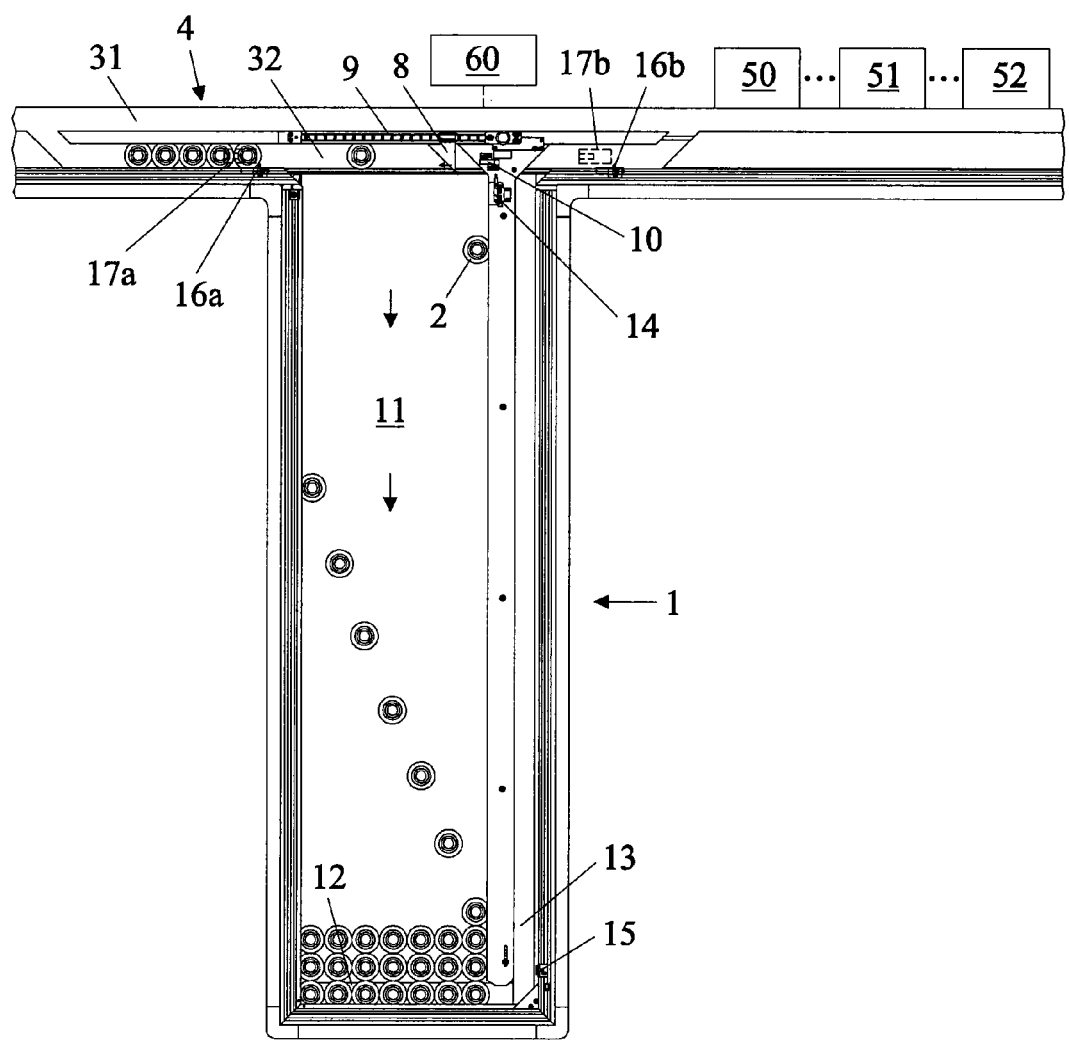
Figure 3:
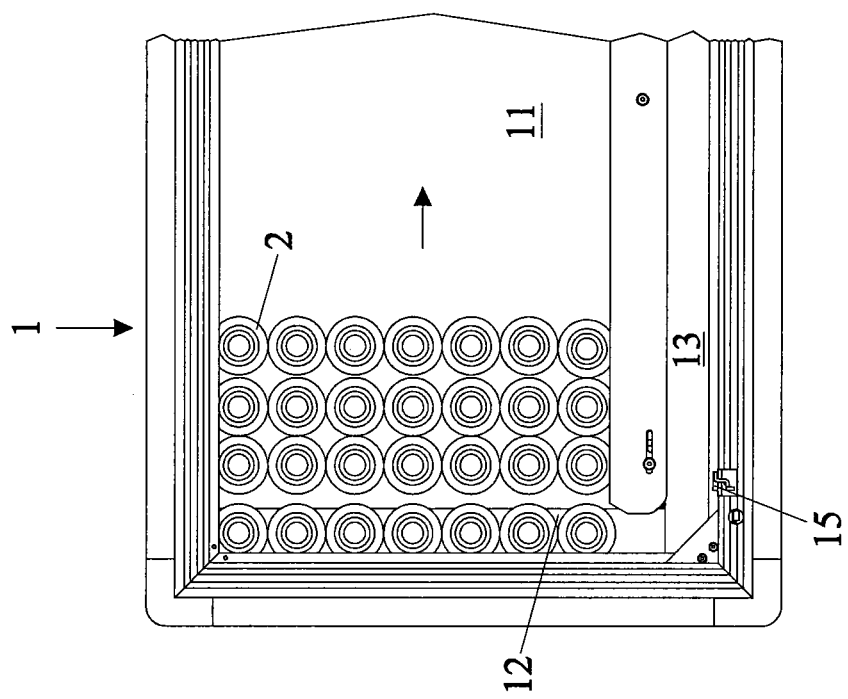
Figure 4:
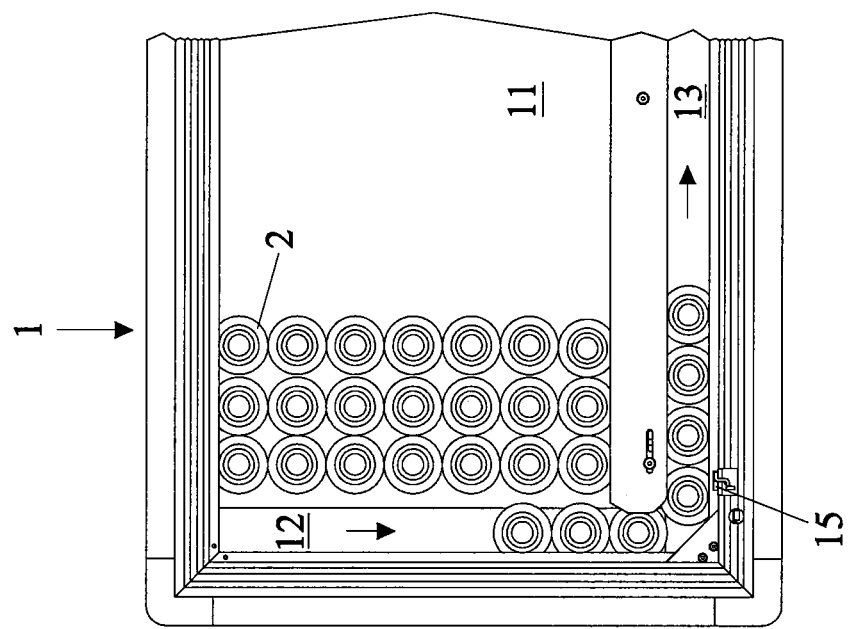
Figure 5:
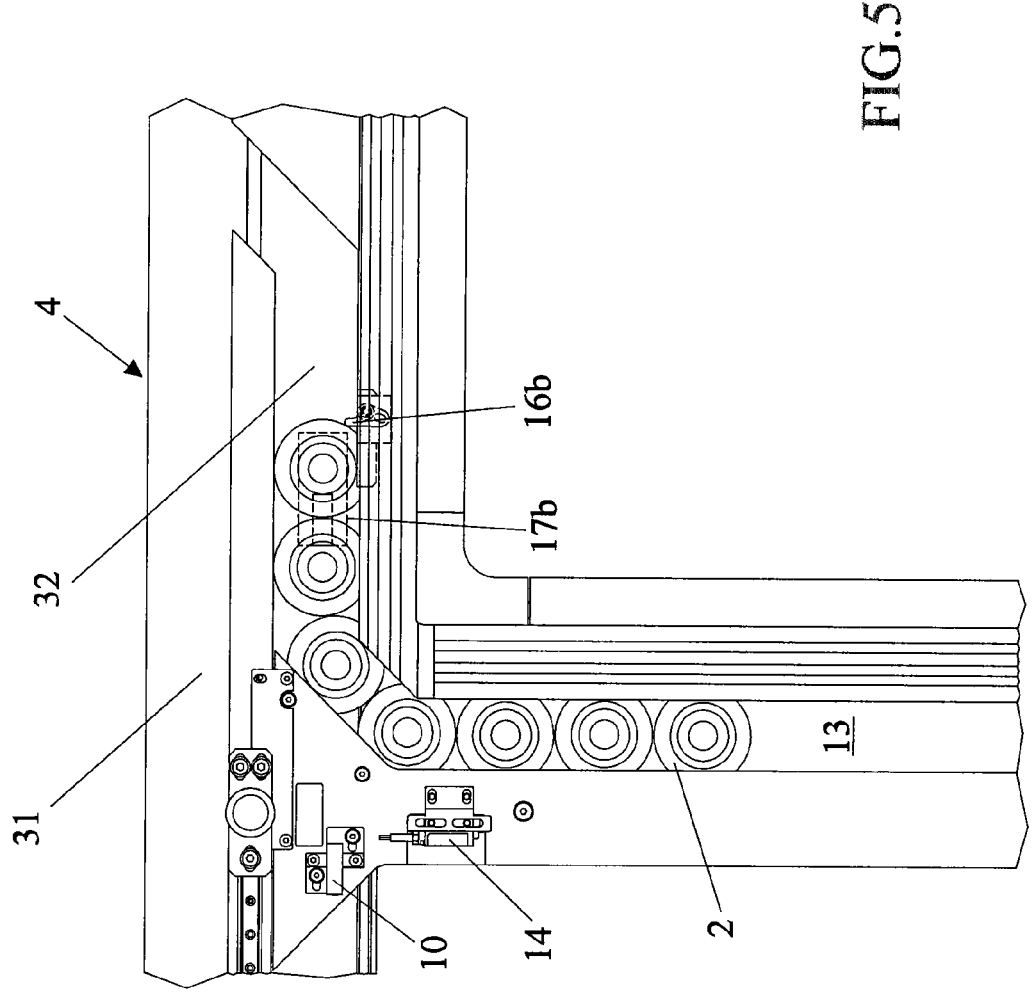

These and other features of the present invention will be further apparent from the following detailed description of one or more embodiments thereof, shown by way of non-limitative example in the accompanying drawings, in which:

FIG. 1 is a perspective view of the entire station interfaced with the laboratory automation system, FIG. 2 is a top view during the step of accumulation of the conveying devices along the station, FIG. 3 shows a top view of a detail of the step of reversing the motion of the main belt and subsequent unpacking of the conveying devices, FIG. 4 shows, again from the top and with the same level of detail as FIG. 3, the channeling of the conveying devices along the return belt, FIG. 5 shows in detail the step of accumulating of the conveying devices near a stop gate after the return belt.

A temporary parking station 1 of conveying devices 2 which travel along a motorized conveyor belt 3, comprising a main lane 31 and a secondary dispatching lane 32, of a laboratory automation system 4 (aimed at identifying, conveying and automatically dispatching the biological material samples), interfaces externally with the laboratory automation system 4, only one portion of which is shown (FIG. 1).

Several stations 1 may be present along the system 4 in a single laboratory, in response to the various packing needs of devices 2, as well as the operative volumes of the laboratory itself. Stations 1 dedicated to parking only empty conveying devices 2 and stations 1 which instead park only full conveying devices 2 (each one accommodating only one container of biological products or test tubes 5) may be advantageously present. Having only one said container of biological products 5 for each conveying device 2 advantageously allows to contribute to increasing testing rapidity in urgent conditions. Station 1 has, in all cases, the same features, and for this reason, by way of example only, FIG. 1 shows conveying devices 2 with test tube 5, while subsequent FIGS. 2-5 show empty conveying devices 2.

A series of modules 50, 51, 52, which may be testing modules or not, are diagrammatically shown. Each module may be ideally preceded by a station 1 (in FIG. 2, for the sake of simplicity, this is shown only with reference to module 50) to respond to the need of not excessively overloading the conveying devices 2 of the module itself; the choice is particularly advantageous in case of testing modules which are particularly slow in processing each single conveying device 2, and thus test tube 5 contained in it, but obviously that the number of stations 1 in each automation system 4 can be determined by variable logical/design choices from system to system.

Appropriately, in addition to the mentioned case in which station 1 is preceded by a slow testing module (in this case, it is clear that station 1 is filled with conveying devices 2 with test tubes 5), other stations 1 could be positioned before non-testing modules, in particular modules used for loading (inputting) samples to the automation system 4. In this case, station 1 accumulates empty conveying devices 2, which once released (according to a logic which will be explained in greater detail below) are associated to test tubes 5 already present in the aforesaid input module.

On software/firmware level, the commands for dispatching the conveying devices 2 stored in the respective station 1 to each of the modules 50, 51, 52 are imparted by a central control unit 60 (FIG. 2) of said automation system 4, i.e. a software program which has the task of establishing whether to control the parking operations and the subsequent release of the conveying devices 2 towards each of the modules or to control the emptying of the conveying devices 2 in/from said station 1.

The conveying devices 2 are, if needed, diverted from the main lane 31 to the dispatching lane 32 of the system 4 by means of a diverting unit 6 (FIG. 1), advantageously similarly to that described in patent application MI2011A002082 by the Applicant; once diverted along the dispatching lane 32, the conveying devices 2 meet a first stop gate 16a (FIG. 2) on said dispatching lane 32, which protrudes laterally from the dispatching lane 32 itself and which blocks conveying devices 2 one at a time, so that they can be detected by a first antenna 17a positioned along the conveyor belt of the dispatching lane 32. Similarly, the conveying devices 2 return from the dispatching lane 32 to the main lane 31 by means of a return lane 7 advantageously similar to that described in the aforesaid patent application. The return unit 7 is preceded by a second stop gate 16b (FIG. 2), also protruding laterally from the dispatching lane 32, and used to temporarily stop the conveying devices 2 waiting to be reintroduced onto the main lane 31, and to allow the simultaneous detection thereof by a second antenna 17b positioned under the conveyor belt of the dispatching lane 32.

On interfacing level between the dispatching lane 32 of the system 4 and the station 1, there is a diverter 8 which can translate horizontally in one direction or the other from a start of travel position to an end of travel position because it is fixed to a motorized belt 9 (FIG. 1, 2) parallel to the dispatching lane 32. An end of travel sensor 10 engages the diverter 8 when it is in the extreme right position (according to the view in FIG. 2) of its movement.

Station 1 comprises a main conveyor belt 11 made of polyurethane which longitudinally conveys the conveying devices 2, diverted in station 1 allowing the accumulation thereof at the end of the station 1 opposite to the interface with the system 4, where a head belt 12 made of the same material is situated, which when activated runs in direction perpendicular to the running direction of the main conveyor belt 11. Said conveying devices (2) thus accumulate in tidy rows on the head belt (12) and on the main conveyor belt (11).

Furthermore, a return belt 13 is present, again made of polyurethane, of width essentially equal to that of the head belt 12, but which runs instead in the same direction as the main conveyor belt 11, but in the opposite sense, i.e. from the bottom of the station 1 toward the system 4. Said head belt 12 runs perpendicularly to said main conveyor belt 11. Said head belt 12 is adapted to convey the conveying devices 2 over the return belt 13 parallel to said main conveyor belt 11. Said return belt 13 is adapted to return the conveying devices 2 over the dispatching lane 32 of the conveyor belt 3.

A main sensor 14 by the side of the main conveyor belt 11, near the interface with the system 4, and a return sensor 15 is further present at the beginning of the return belt 13, i.e. on the end of the station 1 furthermost from the system 4.

Operation is as follows: according to needs to temporarily park conveying devices 2 traveling along the automation system 4 established beforehand by the control unit 60, such devices 2, when they turn up near the diverting unit 6, are diverted from the main lane 31 onto the dispatching lane 32. Said central control unit 60 is adapted to drive the movement of said belts (11, 12, 13).

The description that follows is identical for the stations 1 dedicated to parking conveying devices 2 with test tube 5 and the stations 1 which instead accumulate empty conveying devices 2, according to different needs (previously illustrated) which impose the presence in various points of the system of either one station 1 or the other. As mentioned, FIGS. 2-5 show the case of station 1 with empty conveying devices.

The conveying devices 2 which are diverted form a queue at the first stop gate 16a, which is adapted to queue said conveying devices 2 let into station 1 and to release only one of said conveying devices 2 at each step. From here, the stop gate 16a releases said conveying devices 2 to be dispatched towards station 1 in steps one by one, after reading by the first antenna 17, and preferably with regular frequency. Each of said conveying devices 2, released by the stop gate 16a, continues along said dispatching lane 32. At the same time, the motorized belt 9 is operated in steps adapted to move the diverter 8 in steps leftwards, so as to divert only one of said conveying devices 2 in each step, so that the conveying devices 2 released by the first stop gate 16a are dispatched along the main conveyor belt 11 one after the other, in practice along different dummy lanes. The main conveyor belt 11 is moveable in direction perpendicular to the motorized belt 9. The step movement of the diverter 8 does not occur exactly in the same instants as the timed release of each conveying device 2 from the first gate 16a because it is controlled by the reading of each newly diverted conveying device 2 by said main sensor 14. The main sensor 14 is adapted to activate the translation of said diverter 8.

Said steps of the diverter 8 are timed with said steps of the stop gate 16a. The timing occurs when the first conveying device 2 approaches the first stop gate 16a, as soon as it is read by the first antenna 17a and is released nearly instantaneously; indeed during this step there is no need to synchronize the release with the movement of another component because the diverter 8 stops in the position on the extreme right and does not need to move to divert the conveying device 2 along the dummy lane on the extreme right. The next conveying devices 2 in the queue are instead released by making the first gate 16a appropriately retract in timed manner while the diverter 8 moves in steps leftwards, as described. The diverter 8 is timed so that the step of the diverter 8 occurs as a consequence of the step of the first stop gate 16a after a short period of time and not simultaneously. Said short period of time is calculated according to the speed of the conveyor belt 3 along the dispatching lane 2, because the short period of time needed for the conveying device 2 previously released by the stop gate 16a to reach the diverter 8 and to be diverted onto the main conveyor belt 11 is taken into account. Once the previous conveying device 2 has been diverted, the diverter 8 is in turn made to move by the motorized belt 9 to divert said other conveying device 2.

The result which is obtained is that of a calibrated movement of all the concerned components to ensure a smooth dispatching of the queue of conveying devices 2 along the dummy lanes of the station 1.

FIG. 2 shows precisely a step of such a step movement of the diverter 8, assuming that conveying devices 2 have previously been set aside on the bottom of the station 1.

The number of step movements performed by the device formed by the belt 9 and the diverter 8 are calculated so that, once the diverter 8 reaches its all open start of the travel position (i.e. on the extreme left of the view in FIG. 2) and after the last conveying device 2 of the queue has been dispatched along the dummy lane of the left end, the next step will corresponds to reversing the sense of movement of the belt 9 to put the diverter 8 back in the initial position engaged with the end of travel sensor 10 and waiting for the first conveying device 2 of a next queue formed near the first stop gate 16a.

If conveying devices 2 which do not need to be dispatched to station 1 turn up at the diverting unit 6, they proceed along the main lane 31, i.e. are not diverted.

The conveying devices 2 thus gradually accumulate on the opposite end of the station 1 by virtue of the continuous movement of the main conveyor belt 11 (FIG. 2).

The main conveyor belt 11 is stopped if no new conveying devices 2 are diverted after a given time.

When the station 1 reaches a given filling level, some conveying devices 2 need to be dispatched along the return belt 13 so that they can be then blocked by the stop gate 16b and dispatched more rapidly to the module 50 if needed (we will limit the description to the module 50, considering that each subsequent module 51, 52 could be preceded by a similar station 1, or otherwise a single station 1 could manage the release of the conveying devices 2 towards more than one module).

The first conveying devices 2 to be called up are the ones which were diverted to station 1 first (according to a FIFO, First In First Out, logic).

With this regard, the sense of movement of the main belt 11 is temporarily reversed (FIG. 3); said reversible sense of motion of the main conveyor belt 11 is adapted to unpack the first row of conveying devices 2 which accumulated in tidy rows at said head belt 12, i.e. to create a small space margin between these conveying devices 2 and those arrived afterwards in subsequent rows which would otherwise press against the conveying devices 2 preventing smooth movement.

At this point, this system is ready to eject the row of unpacked conveying devices 2 from the bottom of station 1: the return belt 13 is firstly activated, the movement of the main belt 11 is blocked and then the head belt 12 is activated (FIG. 4). Therefore, the main conveyor belt 11 and the head belt 12 operate alternatively. The conveying devices 2, the number of which is equal to that of the dummy lanes along the main belt 11, thus pass from the head belt 12 to the return belt 13 and, at the end of the path around it, are blocked at the second stop gate 16b, where the first device 2 is detected by the second antenna 17b (FIG. 5).

The head belt 12 is then blocked and at the same time the normal forward rotation of the main belt 11 is restarted so that a new row of conveying devices 2 can be positioned on the bottom of the station 1.

This dispatching operation of the conveying devices 2 along the return belt 13 to favor the formation of a queue of conveying devices 2 at the second stop gate 16b may be performed cyclically; however, as mentioned, the movement of the main belt 11 must be temporarily reversed and then the belt must be stopped before starting the head belt 12. In this moment, it is essential that no new conveying devices 2 are simultaneously diverted by the system 4 because the main conveyor belt 11 has stopped and therefore the newly diverted new conveying devices 2 would not be appropriately fed towards the bottom of the station 1.

In general, the need is to have a higher number of conveying devices 2 available at the second stop gate 16b at all times. For this reason, the complete filling of the return belt 13 was initially attempted by repeating several cycles to call up the conveying devices 2 from the bottom of the station 1. The total filling station of the return belt 13 is discriminated in that the return station 15 is engaged fixed to the conveying device 2 which is last along the queue formed along the return belt 13. Said return sensor 15 is adapted to detect the filling of said return belt 13.

Obviously, until such a situation persists, no other conveying devices 2 can be dispatched to the return belt 13, i.e. the head belt 12 cannot be activated, because the return belt 13 is completely full.

The conveying devices 2 blocked at the second stop gate 16*b* may be re-introduced at any time into the system 4 passing from the return unit 7, with release times determined by the control unit 60 according to the need of the conveying devices 2 of the module 50. The conveying devices 2 are released one at a time through the second gate 16*b*, so that it blocks each one of them even only for a few instants, allowing identification by the second antenna 17*b*.

Typically, the request for conveying devices 2 to be dispatched to the module 50 is not higher than the number of devices 2 queuing along the completed filled return belt 13; the action of blocking each of the conveying devices 2 to be released from the second stop gate 16*b* is functional to a count of the conveying devices 2, and thus only the number of conveying devices 2 actually needed by the module 50 is released.

By virtue of the count above, the station 1 can determine when a number of conveying devices 2 equal to that of the dummy lanes formed along the main conveyor belt 11, i.e. to the number of conveying devices 2 which are introduced along the return belt 13 at each new cycle, was released from the second stop gate.

As a consequence of this, as soon as the counter reaches this number, the station 1 is activated to introduce new conveying devices 2 immediately onto the return belt 13 to replace those which have just left it (in the meantime, the return belt 13 did not stop and consequently the conveying devices 2 already queuing are advanced towards the second gate 16*b*).

This implies that, only at this point, the unpacking operation is restarted (the motion of the main conveyor belt 11 is reversed) and subsequently the head belt 12 is restarted.

It is thus clear that, even in the case of an enormous request for conveying devices 2 by the central control unit 60, station 1 can also complete the request because the return belt 13 will be maintained essentially always full.

After a given period of time has elapsed without new requests by the control unit 60, and thus without new ejections of conveying devices 2 by the second gate 16*b*, the return belt 13 may also be stopped providing it is full or in all cases cannot accommodate a complete new row of conveying devices.

It is clear that the most diverse gradual filling conditions of the main belt 11 and of the return belt 13 can be created according to the requests of the control unit 60 and the number of conveying devices 2 transiting along the automation system.

In all cases, as mentioned, it is attempted to keep the return belt 13 as full of conveying devices 2 as possible, also independently from the immediate arrival of new request from the central control unit 60, and thus call up the conveying devices 2 from the bottom of the station 1 as soon as possible.

The main sensor 14 can detect the total filling of the main belt 11, in addition to picking up as mentioned the passage of each conveying device 2 newly diverted from the diverter: this occurs when the main sensor 14 remains engaged in fixed manner, i.e. at the arrival of the first conveying device 2 on the last available row of the main belt 11. In such a situation, the main belt 11 obviously cannot accommodate new conveying devices 2, which consequently cannot be diverted in the station 1 until at least one row of conveying devices 2 is cleared from the bottom of the station (i.e. until the main sensor 14 is released by advancing all the new rows towards the bottom).

The innovative aspect of the invention is thus making one or more temporarily parking stations of conveying devices containing test tubes or not in a laboratory automation system, in which said conveying devices may be dispatched so as to prevent accumulation upstream of modules which process them particularly slowly (and thus by extension in some points along the automation system) or to prevent such conveying devices from circling additionally, and essentially idly, about the automation system.

In particular, the station may be used to park both conveying devices with test tubes waiting to be processed in a subsequent testing module and conveying devices without test tube to be dispatched later to a loading (input) module of samples along the automation system.

With respect to the known storage areas, which are bulky and very costly, the described solution is easier to implement, i.e. many parking stations may be arranged in different points of the automation system, ideally before each slow test module or input module.

In this manner, when one of the concerned modules is cleared and can thus process new samples, the conveying devices are released from the parking station and rapidly dispatched towards the module, while in the known solutions when the module is cleared the samples are often in an entirely different part of the automation system or stored in an area in all cases far from the module.

The parking station described in this patent in all cases has a large capacity in terms of conveying devices that it can accommodate.

Furthermore, in the case of parking of conveying devices with test tube, it presents the advantage of never separating the test tube from the conveying device which accommodates it during parking; consequently, the association of the conveying device/test tube is never lost during the parking of the devices in the station, unlike what typically occurs in the known storage areas and which may be source of errors.

Furthermore, from the structural point of view the station does not display differences when processing conveying devices with or without test tube and for this reason each station along the system can be used in different moments for either one or the other of the two purposes.

The parking station may be used as area for parking conveying devices also at the end of each working day when the automation system must be switched off.

The invention thus described is susceptible to many changes and variants, all comprised within the scope of the inventive concept.

In practice, the materials used as well as the shapes and size may be any, according to needs.

The invention claimed is:

1. A temporary parking station for conveying devices each containing only one container of biological products, interfacing with a laboratory automation system, comprising a conveyor belt with at least one dispatching lane for said conveying devices, wherein it includes at said dispatching lane a stop gate adapted to queue the conveying devices let into the station and to release only one of said conveying devices at each step, said conveying device proceeding along said dispatching lane to a diverter fitted on a motorized belt, parallel to the dispatching lane, adapted to move said diverter in steps in either one direction or the other from a start of travel position to an end of travel position, said steps of the diverter being timed with said steps of the stop gate, said diverter being adapted to divert for each of said steps only one of said conveying devices on a main conveyor belt moveable in a direction perpendicular to the motorized belt, said main conveyor belt being adapted to convey the conveying devices over a head belt, said conveying devices accumulating in tidy rows on the head belt and on the main conveyor belt, said head belt sliding perpendicularly to said main conveyor belt and being adapted to convey the conveying devices over a return belt parallel to said main conveyor belt and sliding in opposite direction, adapted to return the conveying devices over the dispatching lane of the conveyor belt.

2. The station according to claim 1, wherein said main conveyor belt has a reversible direction of motion to unpack the conveying devices which are accumulated in tidy rows at said head belt.

3. The station according to claim 1 wherein said main conveyor belt and said head belt are alternatively operative.

4. The station according to claim 1, wherein it comprises a main sensor according to claim 1, wherein it comprises a main sensor adapted to activate the translation of said diverter and to detect the total filling of said main conveyor belt and a return sensor adapted to detect the total filling of said return belt.

5. The station according to claim 1, wherein it is driven by a central control unit of said automation system adapted to drive the parking and/or emptying operations of conveying devices in/from said station and thus the movement of said belts.

\* \* \* \* \*